(12) United States Patent
Dai

(10) Patent No.: US 7,887,187 B2
(45) Date of Patent: Feb. 15, 2011

(54) SCALING ZERNIKE COEFFICIENTS TO SMALLER PUPIL SIZES FOR REFRACTIVE TREATMENTS

(75) Inventor: Guang-ming Dai, Fremont, CA (US)

(73) Assignee: AMO Manufacturing USA, LLC., Santa Ana, CA (US)

( * ) Notice: Subject to any disclaimer, the term of this patent is extended or adjusted under 35 U.S.C. 154(b) by 0 days.

(21) Appl. No.: 12/722,881

(22) Filed: Mar. 12, 2010

(65) Prior Publication Data

US 2010/0198567 A1 Aug. 5, 2010

Related U.S. Application Data

(63) Continuation of application No. 11/676,094, filed on Feb. 16, 2007, now Pat. No. 7,717,562.

(60) Provisional application No. 60/776,289, filed on Feb. 24, 2006.

(51) Int. Cl.
*A61B 3/10* (2006.01)
(52) U.S. Cl. ...................................... 351/212; 351/200
(58) Field of Classification Search ................. 351/212
See application file for complete search history.

(56) References Cited

U.S. PATENT DOCUMENTS

| 4,665,913 A | 5/1987 | L'Esperance, Jr. |
| 4,669,466 A | 6/1987 | L'Esperance |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 5,108,388 A | 4/1992 | Trokel |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |
| 5,683,379 A | 11/1997 | Hohla |
| 5,713,892 A | 2/1998 | Shimmick |
| 5,807,379 A | 9/1998 | L'Esperance, Jr. |

(Continued)

FOREIGN PATENT DOCUMENTS

WO    WO 02/098290 A    12/2002

(Continued)

OTHER PUBLICATIONS

Bara, Salvador et al. "Direct Transformation of Zernike Eye Aberration Coefficients Between Scaled, Rotaed, and/or Displaced pupils", Journal of the Optical Society of America, 2006, vol. 23, No. 9, Sep. 2006, pp. 2061-2066.

(Continued)

*Primary Examiner*—Jordan M. Schwartz
*Assistant Examiner*—James C Jones

(57) ABSTRACT

Wavefront measurements of eyes are normally taken when the pupil is relatively large, and the results are often represented by a set of Zernike coefficients. Different sets of Zernike coefficients can be calculated to represent aberrations at smaller pupil sizes. While recently described techniques allow scaling of the expansion coefficients with Zernike polynomials, a more intuitive approach would be desirable. Such an approach may optionally derive an equivalent result as known techniques, but may employ a much simpler and non-recursive formula between the new and the original sets of Zernike polynomial expansion coefficients of a wavefront when the aperture size is scaled.

20 Claims, 6 Drawing Sheets

U.S. PATENT DOCUMENTS

| | | | |
|---|---|---|---|
| 6,004,313 | A | 12/1999 | Shimmick et al. |
| 6,095,651 | A | 8/2000 | Williams et al. |
| 6,203,539 | B1 | 3/2001 | Shimmick et al. |
| 6,271,915 | B1 | 8/2001 | Frey et al. |
| 6,315,413 | B1 | 11/2001 | Shimmick et al. |
| 6,331,177 | B1 | 12/2001 | Munnerlyn et al. |
| 7,293,873 | B2 | 11/2007 | Dai et al. |
| 7,434,936 | B2 | 10/2008 | Dai et al. |
| 7,695,136 | B2 | 4/2010 | Dai |
| 7,717,562 | B2 | 5/2010 | Dai |
| 2003/0225399 | A1 | 12/2003 | Chernyak et al. |
| 2004/0169820 | A1 | 9/2004 | Dai et al. |
| 2005/0270491 | A1 | 12/2005 | Dai et al. |
| 2007/0058132 | A1* | 3/2007 | Dai ............ 351/246 |
| 2008/0117231 | A1 | 5/2008 | Kimpe |
| 2008/0198331 | A1 | 8/2008 | Azar et al. |
| 2009/0036980 | A1 | 2/2009 | Norrby et al. |
| 2009/0086163 | A1 | 4/2009 | Dai et al. |

FOREIGN PATENT DOCUMENTS

| | | | |
|---|---|---|---|
| WO | WO 2004/113958 | A | 12/2004 |

OTHER PUBLICATIONS

Campbell, Charles E., "Matrix Method to Find a New Set of Zernike Coefficients From an Original Set When the Aperture Radius is Changed", Journal of the Optical Society of America, 2003, vol. 20, No. 2, Feb. 2003, pp. 209-217.

Dai, Guang-Ming, "Scaling Zernike Expansion Coefficients to Smaller Pupil Sizes: A Simpler Formula", Journal of the Optical Society of America, 2006, vol. 23, No. 3, Mar. 2006, pp. 539-543.

Goldberg, Kenneth et al., "Wave-Front Measurement Errors From Restricted Concentric Subdomains", Journal of the Optical Society of America, 2001, vol. 18, No. 9, Sep. 2001, pp. 2146-2152.

Guirao, Antonio et al., "Effect of Rotation and Translation on the Expected Benefit of an Ideal Method to Correct the Eye's Higher-Order Aberrations", Journal of the Optical Society of America, 2001, vol. 18, No. 5, May 2001, pp. 1003-1015.

Janssen, Augustus et al., "Concise Formula for the Zernike Coefficients of Scaled Pupils", Journal of Microlithography, Microfabrication, and Microsystems, Jul.-Sep. 2006/vol. 5(3), pp. 30501-1 to 30501-3.

Lundstrom, Linda et al., "Transformation of Zernike Coefficients: Scaled, Translated, and Rotated Wavefronts With Circular and Elliptical Pupils", Journal of the Optical Society of America, vol. 24, No. 3, Mar. 2007, pp. 569-577.

Schweigerling, Jim, "Scaling Zernike expansion coefficients to different pupil sizes", Journal of the Optical Society of America, 2002, vol. 19, No. 10, Oct. 2002, pp. 1937-1945.

Shu, Huazhong et al., "General Method to Derive the Relationship Between Two Sets of Zernike Coefficients Corresponding to Different Aperature Sizes", Journal of the Optical Society of America, 2006, vol. 23, No. 8, Aug. 2006, pp. 1960-1966.

Wilson, M. A. et al., "The Julius F. Neumueller Award in Optics, 1989: Change of Pupil Centration with Change of Illumination and Pupil Size", Optom. and Vis. Sci., 69, No. 2 : 129-136 (1992).

Yang, Yabo et al., "Pupil Location Under Mesopic, Photopic, and Pharmacological Dilated Conditions", Investigative Opthalmalogy & Visual Science, Jul. 2002, vol. 43, No. 7, pp. 2508-2512.

* cited by examiner

US 7,887,187 B2

SCALING ZERNIKE COEFFICIENTS TO SMALLER PUPIL SIZES FOR REFRACTIVE TREATMENTS

CROSS REFERENCE TO RELATED APPLICATIONS

This application is a continuation of U.S. patent application Ser. No. 11/676,094, filed Feb. 16, 2007, which claims the benefit of U.S. Provisional Application No. 60/776,289, filed Feb. 24, 2006, the disclosure of which is incorporated herein by reference.

BACKGROUND OF THE INVENTION

A recent recursive analytical formula has been derived to calculate a set of new Zernike polynomial expansion coefficients from an original set when the size of the aperture is reduced. There may be benefits to a more intuitive derivation of a simpler, nonrecursive formula, which can be used to calculate the instantaneous refractive power.

BRIEF SUMMARY OF THE INVENTION

The ocular aberrations of human eyes can now be measured objectively thanks to the introduction of wavefront technology to opthamology. In the various fields of optics, wavefront aberrations have traditionally been represented by Zernike polynomials.

Wavefront measurements of eyes are normally taken when the pupil is relatively large, and the results are often represented by a set of Zernike coefficients. Different sets of Zernike coefficients can be calculated to represent aberrations at smaller pupil sizes. While recently described techniques allow scaling of the expansion coefficients with Zernike polynomials, a more intuitive approach would be desirable. Such an approach may optionally derive an equivalent result as known techniques, but may employ a much simpler and nonrecursive formula between the new and the original sets of Zernike polynomial expansion coefficients of a wavefront when the aperture size is scaled.

In a first aspect, embodiments of the present invention provide a method of calculating a modified normalized Zernike expansion coefficient for an optical system. The method may include inputting an original normalized Zernike expansion coefficient for the optical system, where the original normalized Zernike expansion coefficient is associated with a first aperture dimension. The method may also include calculating a modified normalized Zernike expansion coefficient for the optical system, where the modified normalized Zernike expansion coefficient is associated with a second aperture dimension. In some cases, the modified normalized Zernike expansion coefficient can be calculated based on the original normalized Zernike expansion coefficient scaled by a scaling factor. The scaling factor can include a ratio of the second aperture dimension to the first aperture dimension, where the ratio raised to the power of a factor comprising a radial degree of the coefficient. In some cases, the aperture dimension includes an aperture radius. In some cases, the optical system include an optical tissue of a patient, and the aperture dimension includes a pupil dimension. In some cases, the pupil dimension includes a pupil radius. Optionally, the first aperture dimension may be greater than the second aperture dimension.

In another aspect, embodiments of the present invention provide a method of determining an optical surface model for an optical tissue system of an eye. The method can include inputting a first optical data corresponding to the optical tissue system of the eye, where the first optical data includes a first set of normalized Zernike expansion coefficients corresponding to a first pupil radius of the eye. The method can also include calculating a second optical data corresponding to the optical tissue of the eye, where the second optical data includes a second set of normalized Zernike expansion coefficients corresponding to a second pupil radius of the eye. The second set of normalized Zernike expansion coefficient can be calculated based on the first set of normalized Zernike expansion coefficients scaled by a scaling factor. The scaling factor can include a ratio of the second aperture dimension to the first aperture dimension. The ratio can be raised to the power of a factor that includes a radial degree of the coefficient. The method can further include determining the optical surface model based on the second optical data. Optionally, the first pupil radius of the eye can be greater than the second pupil radius of the eye.

In another aspect, embodiments of the present invention provide a system for calculating a modified normalized Zernike expansion coefficient for an optical system. The system can include, for example, means for inputting an original normalized Zernike expansion coefficient for the optical system, where the original normalized Zernike expansion coefficient is associated with a first aperture dimension. The system can also include means for calculating a modified normalized Zernike expansion coefficient for the optical system, where the modified normalized Zernike expansion coefficient is associated with a second aperture dimension. The modified normalized Zernike expansion coefficient can be calculated based on the original normalized Zernike expansion coefficient scaled by a scaling factor. The scaling factor can include a ratio of the second aperture dimension to the first aperture dimension, where the ratio raised to the power of a factor comprising a radial degree of the coefficient. The aperture dimension can include an aperture radius. In some cases, the optical system includes an optical tissue of a patient, and the aperture dimension includes a pupil dimension. Optionally, the pupil dimension may include a pupil radius. In some cases, the first aperture dimension is greater than the second aperture dimension.

In another aspect, embodiments of the present invention provide a method of calculating effective powers of an optical system. The method can include, for example, calculating a first effective power using a first Zernike expansion coefficient for the optical system, where the first Zernike expansion coefficient is associated with a first aperture dimension. The method can also include calculating a second effective power using a second Zernike expansion coefficient for the optical system, where the second Zernike expansion coefficient is associated with a second aperture dimension. The second Zernike expansion coefficient can be scaled relative to the first Zernike expansion coefficient using a scaling factor that includes a ratio of the second aperture dimension to the first aperture dimension raised to a power of a factor that includes a radial degree of the coefficient. In some cases, the optical system includes an optical tissue of a patient, and the aperture dimension includes a pupil dimension. In some cases, the pupil dimension includes a pupil radius.

In another aspect, embodiments of the present invention provide a system for calculating effective power for an optical system. The system can include means for inputting first Zernike expansion coefficient for the optical system, where the first Zernike expansion coefficient is associated with a first aperture dimension. The system can also include means for calculating a second effective power using a second Zernike expansion coefficient for the optical system, where the second Zernike expansion coefficient is associated with a second aperture dimension and scaled relative to the first Zernike expansion coefficient using a scaling factor that includes a ratio of the second aperture dimension to the first aperture dimension raised to a power of a factor that includes a radial degree of the coefficient. In some cases, the optical system includes an optical tissue of a patient, and the aperture dimension includes a pupil dimension. In some cases, the pupil dimension includes a pupil radius.

In a further aspect, embodiments of the present invention provide a computer program product for determining an optical surface model for an optical tissue system of an eye. The computer program product can include, for example, code for accepting a first optical data corresponding to the optical tissue system of the eye, where the first optical data includes a first set of normalized Zernike expansion coefficients corresponding to a first pupil radius of the eye. The product can also include code for calculating a second optical data corresponding to the optical tissue of the eye, where the second optical data includes a second set of normalized Zernike expansion coefficients corresponding to a second pupil radius of the eye. According to code, the second set of normalized Zernike expansion coefficient can be calculated based on the first set of normalized Zernike expansion coefficients scaled by a scaling factor. The scaling factor can include a ratio of the second aperture dimension to the first aperture dimension, and the ratio can be raised to the power of a factor comprising a radial degree of the coefficient, the product can also include code for determining the optical surface model based on the second optical data. Optionally, the product includes a computer-readable medium for storing the codes. In some cases, the optical system includes an optical tissue of a patient, and the aperture dimension includes a pupil dimension.

For a fuller understanding of the nature and advantages of the present invention, reference should be had to the ensuing detailed description taken in conjunction with the accompanying drawings.

DETAILED DESCRIPTION OF THE INVENTION

The present invention can be readily adapted for use with existing laser systems, wavefront measurement systems, and other optical measurement devices. While the systems, software, and methods of the present invention are described primarily in the context of a laser eye surgery system, it should be understood the present invention may be adapted for use in alternative eye treatment procedures and systems such as spectacle lenses, intraocular lenses, contact lenses, corneal ring implants, collagenous corneal tissue thermal remodeling, and the like.

Figure 1:
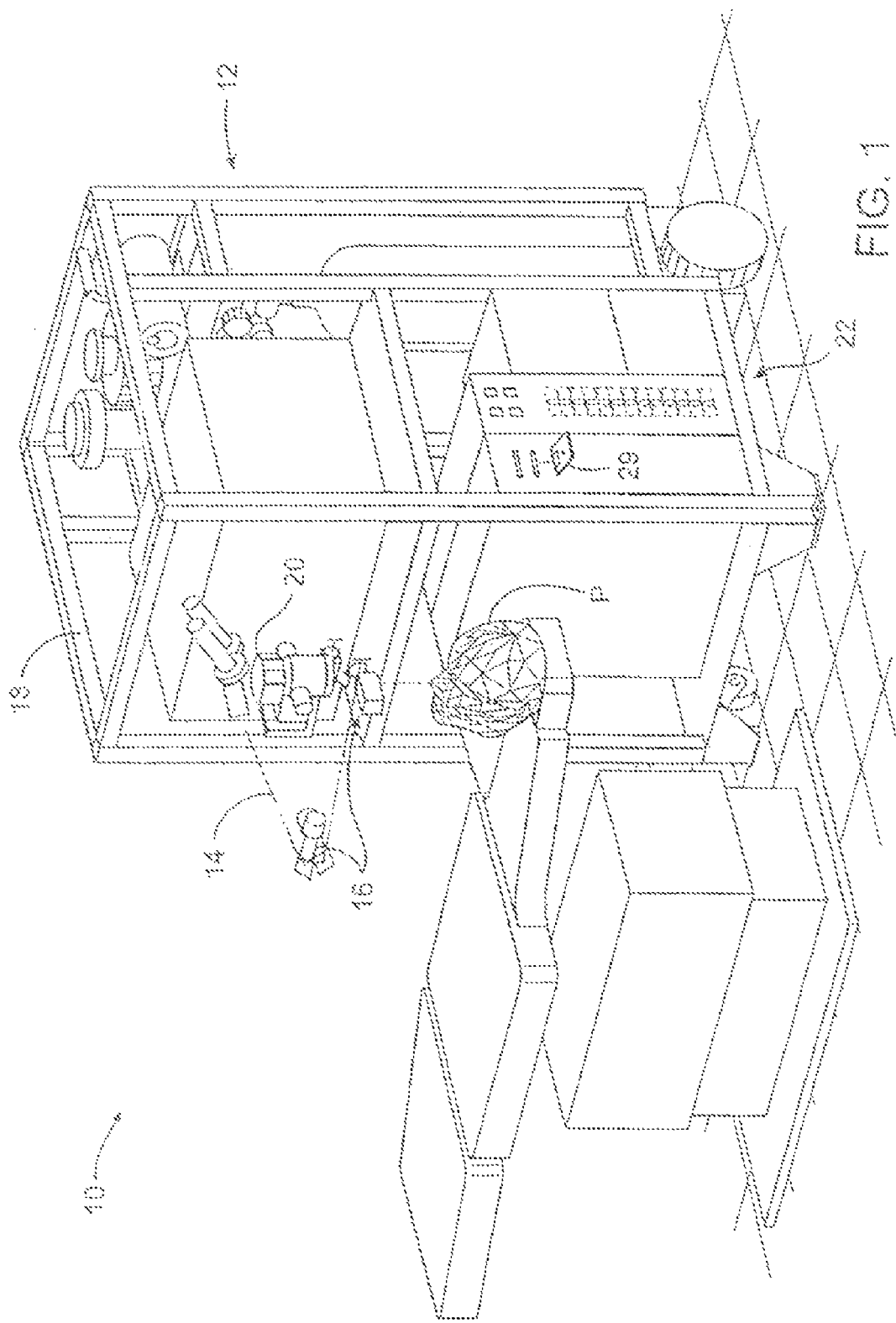
FIG. 1 illustrates a laser ablation system which may be included or used with an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
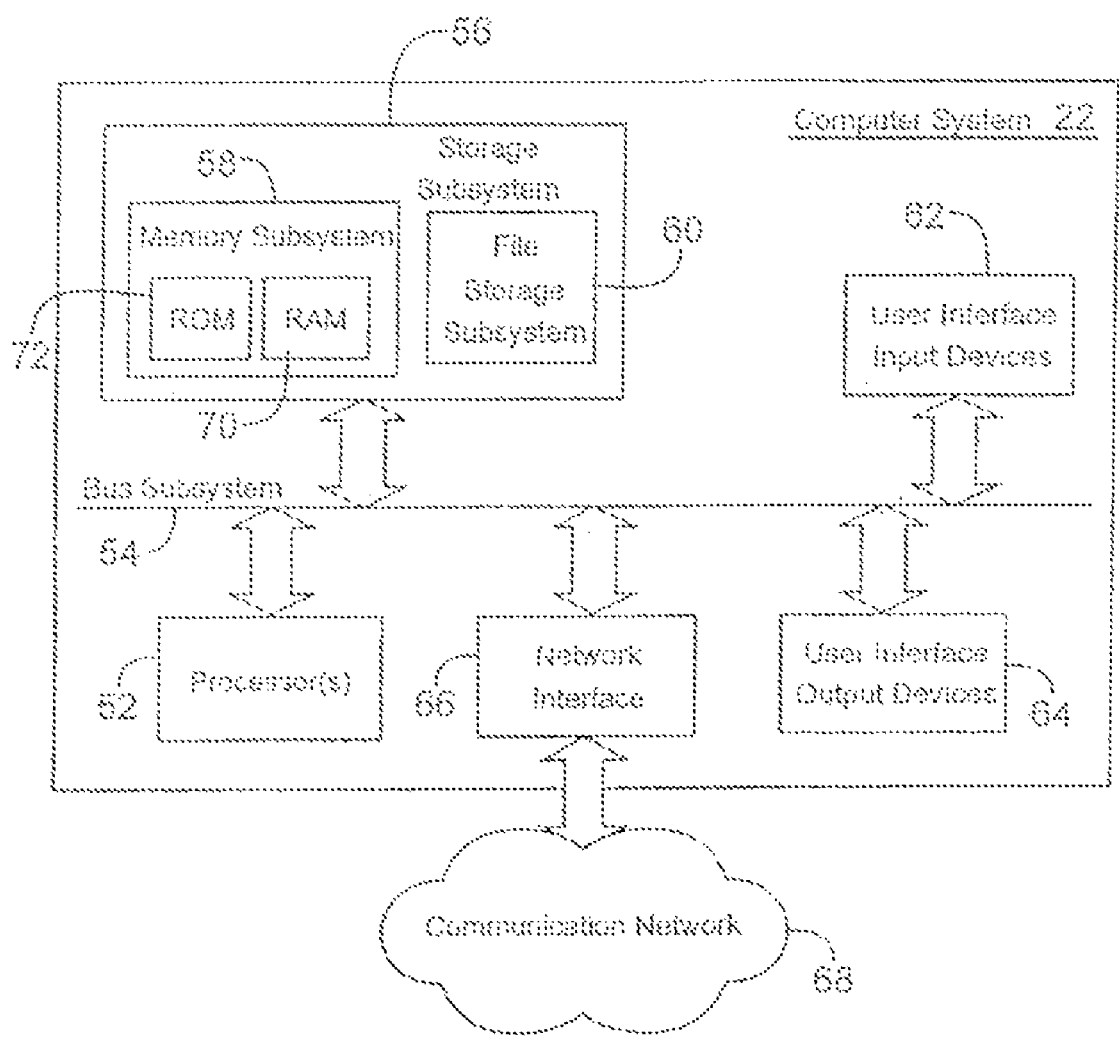
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wave front measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R. CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
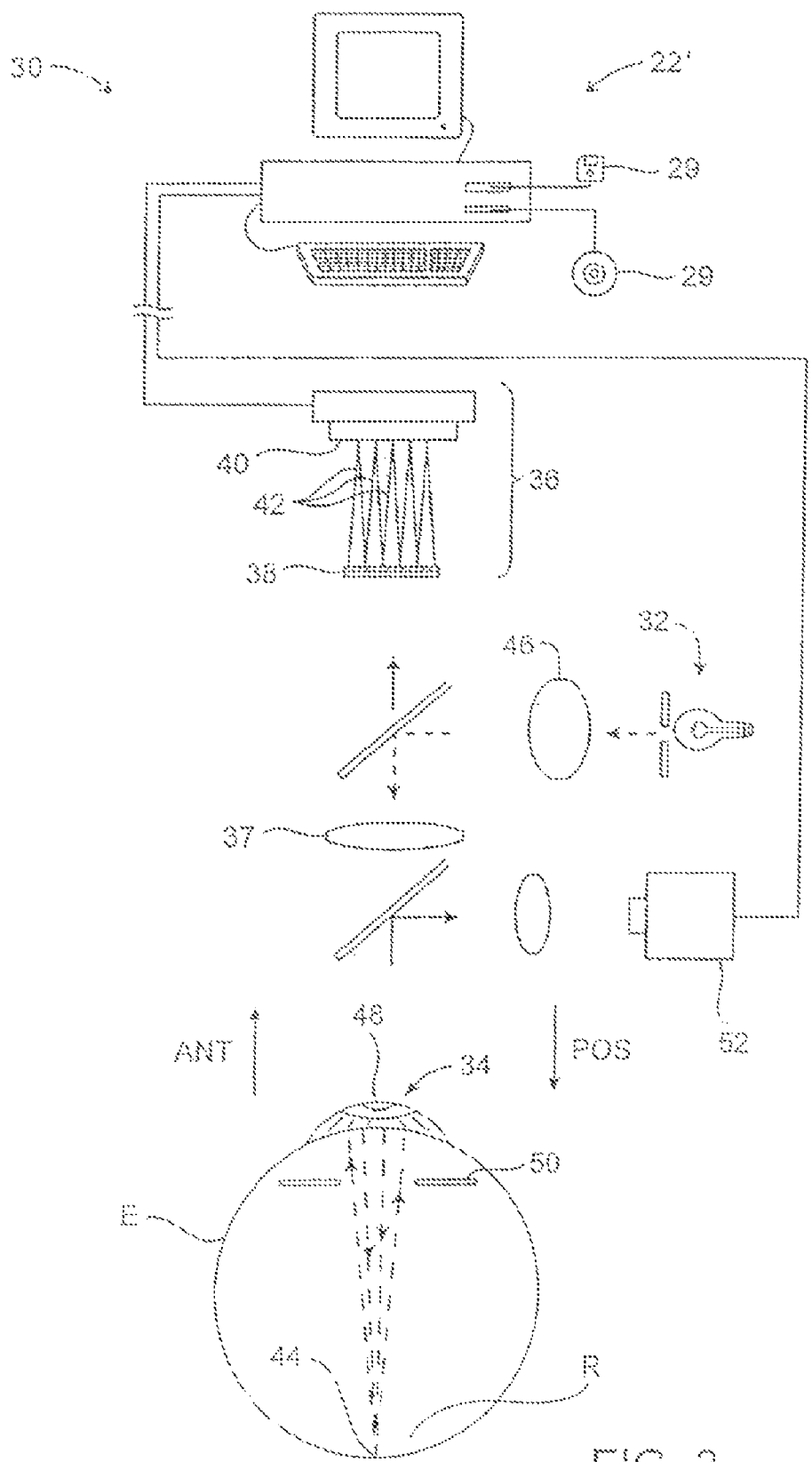
FIG. 3 illustrates a wavefront measurement system according to an embodiment of the present invention.

Referring now to FIG. 3 one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 52 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
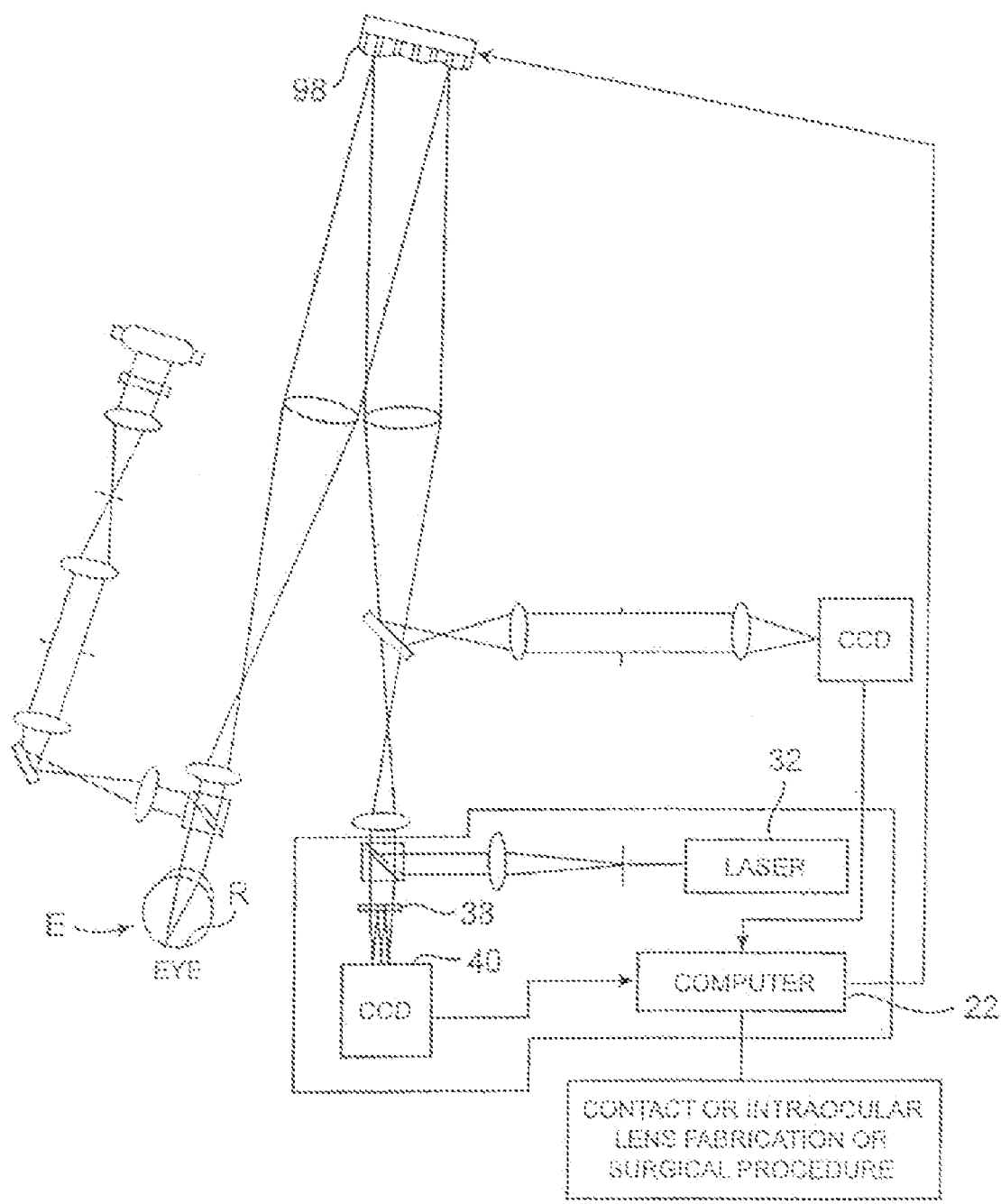
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 98 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a VISX WaveScan® system, available from VISX, INCORPORATED of Santa Clara, Calif. One embodiment includes a WaveScan® with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention.

Figure 4:
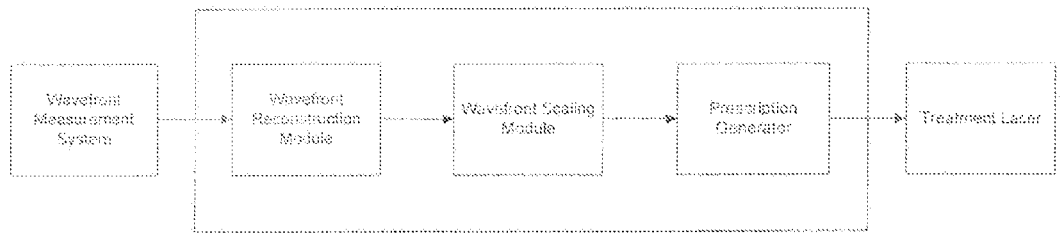
FIG. 4 is a schematic block diagram illustrating software and/or hardware modules which may be included in the computer system of FIG. 2 for use in embodiments of the invention.
Figure 5:
FIG. 5 is a flowchart schematically illustrating an embodiment of a method of the invention.

FIGS. 4 and 5 schematically illustrate embodiments of hardware and/or software modules of computer system 22 and a related method, respectively. These embodiments can generate scaled wavefront reconstruction data suitable for analysis of a patient's eye when a pupil of the patient changes size from a relatively large wavefront measurement pupil size to a smaller size. Structures and methods for reconstructing a wavefront and/or generating prescriptions from wavefront data are well documented in a variety of patent literature, including U.S. patent application Ser. Nos. 10/738,358, as filed on Dec. 5, 2003 and entitled "Presbyopia Correction Using Patient Data;" and 11/134,630, as filed on May 19, 2005 and entitled "Residual Accommodation Threshold for Correction of Presbyopia and Other Presbyopia Correction Using Patient Data," the full disclosures of which are incorporated herein by reference. The following description will address scaling of the wavefront data, particularly scaling of Zernike polynomial expansion coefficients of a wavefront so as to accommodate or model constriction of the pupil of the patient when viewing objects under different lighting conditions, differing viewing distances, and the like.

If $W(Rr, \theta)$ represents the ocular aberrations of a human eye measured as the optical path difference, the wavefront can be decomposed into a set of complete and orthogonal basis functions as:

$$W(Rr, \theta) = \sum_{i=0}^{\infty} a_i F_i(r, \theta), \quad \text{(Eq. 1)}$$

where $a_i$ is the coefficient of the ith basis function $F_i(r, \theta)$ and R is the pupil radius. Here, r is the radial variable in the polar coordinates defining the unit circle. Zernike polynomials have been widely used as a set of basis functions because of their connection to classical aberrations in optical systems with circular apertures.

The normalized Zernike polynomials may be defined as:

$$Z_i(r, \theta) = R_n^{|m|}(r) \theta^m(\theta), \quad \text{(Eq. 2)}$$

where n and m denote the radial degree and the azimuthal frequency, respectively; the radial polynomials are defined as:

$$R_n^{|m|}(r) = \sum_{s=0}^{(n-|m|)/2} \frac{(-1)^s \sqrt{n+1} (n-s)!}{s! [(n+m)/2 - s]! [(n-m)/2 - s]!} r^{n-2s} \quad \text{(Eq. 3)}$$

and the triangular functions as:

$$\theta^m(\theta) = \begin{cases} \sqrt{2} \cos|m|\theta & (m > 0) \\ 1 & (m = 0) \\ \sqrt{2} \sin|m|\theta & (m < 0) \end{cases} \quad \text{(Eq. 4)}$$

Both the single-index i and the double-index m and n may be referred to herein. These two different indexing schemes can be effectively identical. For example, the decision whether to use a single or double index may be based on convenience.

It can be usefully assumed that (1) the optical properties of the human eye do not change when the pupil constricts and (2) the constriction of the pupil is concentric.

Figure 6A:
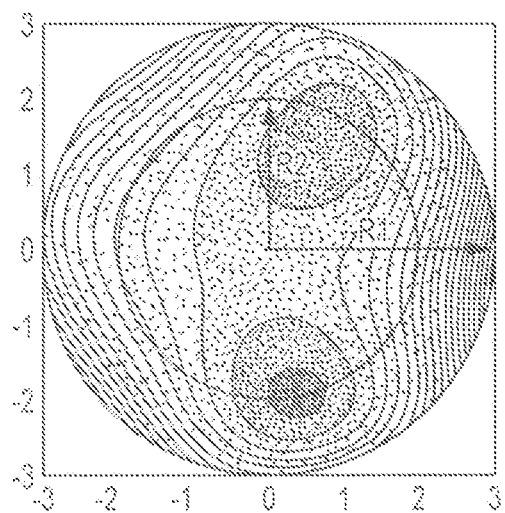
FIGS. 6A and 6B are contour plots of a wavefront at two different pupil sizes.
Figure 6B:
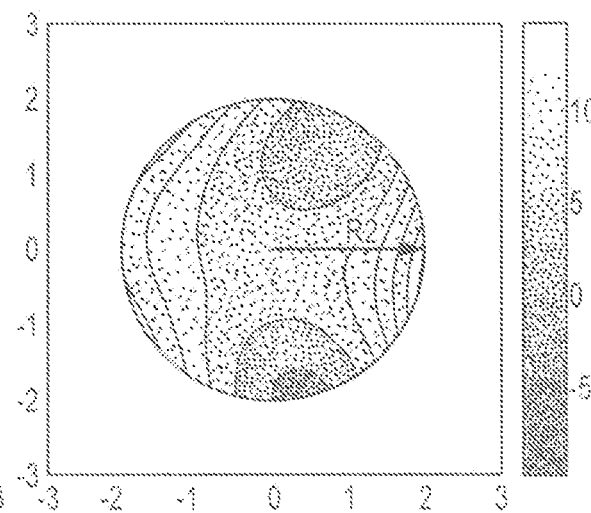

Assume that the pupil aperture changes from $R_1$ to $R_2$, as shown in FIGS. 6A and 6B. The ocular aberrations of the pupil with the smaller radius, $R_2$, are the same as the aberrations of the area defined by radius $R_2$ when the pupil size is $R_1$; i.e., the aberrations do not change when the pupil size changes.

FIGS. 6A and 6B graphically illustrate contour plots of a wavefront map with pupil radius $R_1$ (in FIG. 6A) and the wavefront map when the pupil size constricts to pupil radius $R_1$ to $R_2$ (in FIG. 6B). The two maps are in the same scale. Units are in micrometers of optical path difference. Note that the portion of the wavefront defined by $R_2$ in FIG. 6A is the same as the plot in FIG. 6B.

If $F_i(r, \theta)$ is replaced by Zernike polynomials $Z_i(r, \theta)$ in Eq. (1), the entire wavefront over the pupil with radius $R_1$ can be written as:

$$W_1(R_1 r, \theta) = \sum_{i=0}^{\infty} a_i Z_i(r, \theta), \quad \text{(Eq. 5)}$$

where $a_i$ is the ith Zernike coefficient representing the Zernike expansion into the pupil when the pupil radius is $R_1$. Similarly, the entire wavefront over the pupil with radius $R_2$ can be written as:

$$W_2(R_2 r, \theta) = \sum_{i=0}^{\infty} b_i Z_i(\in r, \theta), \quad \text{(Eq. 6)}$$

where $b_i$ is the ith Zernike coefficient representing the Zernike expansion into the pupil when the pupil radius is $R_2$. The next step is to determine the relationship of $\{b_i\}$ to $\{a_i\}$.

From Eq. (5), to represent only the area defined by radius $R_2$, $W'_1(R_1 r, \theta)$, only r (which runs from 0 to 1) needs to be scaled by a scaling factor of $\epsilon r$, which runs from 0 to $\epsilon$. Therefore, $$W'_1(R_1 r, \theta) = \sum_{i=0}^{\infty} a_i Z_i(\epsilon r, \theta) \qquad \text{(Eq. 7)}$$

As shown in FIGS. 6A and B, it is known that $$W'_1(R_1 r, \theta) = W_2(R_2 r, \theta). \qquad \text{(Eq. 8)}$$

And so, from Eqs. (6)-(8), it is found that $$\sum_{i=0}^{\infty} b_i Z_i(r, \theta) = \sum_{i=0}^{\infty} a_i Z_i(\epsilon r, \theta). \qquad \text{(Eq. 9)}$$

Derivation of Eq. (9) comes from the definition of wavefront expansion into basis functions. Equation (9) can be applied to any set of basis functions. If the triangular function is the same in both sides of Eq. (9), i.e., there is no rotation, after Eq. (2) is applied the relationship between the sets of coefficients $\{a_i\}$ and $\{b_i\}$ is $$\sum_n \sum_m b_n^m R_n^{|m|}(r) = \sum_n \sum_m a_n^m R_n^{|m|}(\epsilon r). \qquad \text{(Eq. 10)}$$

Substituting $R_n^m(r)$ from Eq. (3) to Eq. (10) yields $$\sum_{n=0}^{N} \sum_m b_n^m \sum_{s=0}^{(n-|m|)/2} \frac{(-1)^s \sqrt{n+1} (n-s)! r^{n-2s}}{s![(n+m)/2-s]![(n-m)/2-s]!} =$$

$$\sum_{n=0}^{N} \sum_m a_n^m \sum_{s=0}^{(n-|m|)/2} \frac{(-1)^s \sqrt{n+1} (n-s)! \epsilon^{n-2s} r^{n-2s}}{s![(n+m)/2-s]![(n-m)/2-s]!}, \qquad \text{(Eq. 11)}$$

where N is the total number of orders used for the expansion. Expanding this equation into a radial series yields radial powers of r from 0 to N, resulting in (N+1) equations. This leads to a solution for (N+1) relations between $a_n^m$ and $b_n^m$.

Going from top to bottom for radial powers of r in Eq. (11), consider the $r^N$ case. We get $r^N$ terms only when n=N and s=0. Then Eq. (11) results in $$b_N^m = \epsilon^N a_N^m. \qquad \text{(Eq. 12)}$$

Similarly, for the $r^{N-1}$ case, we get the terms only when n=N−1 and s=0. Then Eq. (11) yields $$b_{N-1}^m = \epsilon^{N-1} a_{N-1}^m \qquad \text{(Eq. 13)}$$

To obtain a general solution, consider the order n with azimuthal frequency m. So far $r^n$, we know that s=0 for order n, s=1 for order n+2, s=2 for order n+4, . . . , or s=(N−n)/2 for order n+2[(N−n)/2] can have the radial order of $r^n$. Hence, $$\sum_{i=0}^{(N-n)/2} b_{n+2i}^m \frac{(-1)^i \sqrt{n+2i+1} (n+i)! r^n}{i![(n+2i+m)/2-i]![(n+2i-m)/2-i]!} = \qquad \text{(Eq. 14)}$$

$$\sum_{i=0}^{(N-n)/2} a_{n+2i}^m \frac{(-1)^i \sqrt{n+2i+1} (n-i)! \epsilon^n r^n}{i![(n+2i+m)/2-i]![(n+2i-m)/2-i]!},$$

In Eq. (14), index i was used to prevent confusion with index s used in Eq. (11), although both i and s have the same summation structure. Because Eq. (14) was derived for $r^n$ only, in can be any integer from −n to n with a step of 2.

Because the denominators at both sides of Eq. (14) are the same for any given i, then $$\sum_{i=0}^{(N-n)/2} \frac{b_{n+2i}^m}{i!} (-i)^i \sqrt{n+2i+1} (n+i)! = \qquad \text{(Eq. 15)}$$

$$\sum_{i=0}^{(N-n)/2} \frac{\epsilon^n a_{n+2i}^m}{i!} (-1)^i \sqrt{n+2i+1} (n+i)!$$

Expanding i=0 case from Eq. (15), we can obtain a recursive formula as $$b_n^m = \epsilon^n a_n^m + \sum_{i=1}^{(N-n)/2} \frac{(-1)^i}{i!n!} \sqrt{\frac{n+2i+1}{n+1}} (n+i)! (\epsilon^n a_{n+2i}^m - b_{n+2i}^m) \qquad \text{(Eq. 16)}$$

$$= \epsilon^n a_n^m + \sum_{i=1}^{(N-n)/2} \frac{(-1)^i}{i!} \sqrt{(n+2i+1)(n+1)} \times$$

$$(n+i)(n+i-1) \ldots (n+2)(\epsilon^n a_{n+2i}^m - b_{n+2i}^m)$$

$$= \epsilon^n a_n^m + \sum_{i=1}^{(N-n)/2} \frac{(-1)^i (n+i)!}{(n+1)!i!} \sqrt{(n+2i+1)(n+1)} \times$$

$$(\epsilon^n a_{n+2i}^m - b_{n+2i}^m).$$

Equation (16) is the final recursive formula. With the use of Eq. (16) and Eqs. (12) and (13), relations between $\{b_i\}$ and $\{a_i\}$ can be obtained analytically.

To obtain a nonrecursive formula, Eq. (16) is applied to replace $b_{n+2i}^m$. For example, the coefficient of the (n+2)th order can be written as $$b_{n+2}^m = \epsilon^{n+2} a_{n+2}^m + \sum_{i=1}^{(N-n)/2-1} \frac{(-1)^i (n+i+2)!}{(n+3)!i!} \times \qquad \text{(Eq. 17)}$$

$$\sqrt{(n+2i+3)(n+3)} (\epsilon^{n+2} a_{n+2i+2}^m - b_{n+2i+2}^m).$$

With the expansion of $b_{n+2i}^m$ to each order higher than n for $b_{n+2i}$ in Eq. (16) and some laborious arithmetic (see the derivation of Eq. 18 below), a final analytical formula is obtained as $$b_n^m = \epsilon^n \left[ \begin{array}{c} a_n^m + \sum_{i=1}^{(N-n)/2} a_{n+2i}^m \sqrt{n+2i+1)(n+1)} \times \\ \sum_{j=0}^{i} \frac{(-1)^{i+j}(n+i+j)!}{(n+j+1)!(i-j)!j!} \epsilon^{2j} \end{array} \right]. \quad \text{(Eq. 18)}$$

Sometimes it is useful to use unnormalized Zernike polynomials. In this case, Eq. (18) can be derived (see the derivation of Eq. 19 below) as $$b_n^m = \epsilon^n \left[ \begin{array}{c} a_n^m + (n+1) \sum_{i=1}^{(N-n)/2} \\ a_{n+2i}^m \sum_{j=0}^{i} \frac{(-1)^{i+j}(n+i+j)!}{(n+j+1)!(i-j)!j!} \epsilon^{2j} \end{array} \right]. \quad \text{(Eq. 19)}$$

The dioptric power of human eyes is typically the power desired from a thin lens with a uniform optical power to give the subject the best distance vision. This dioptric power may be independent of pupil size. However, if high-order aberrations are present, especially radially symmetrical terms, dioptric power can change when pupil size changes. The instantaneous power that is dependent on pupil size is herein called effective power.

Because of the aberration-balancing nature of Zernike polynomials, all symmetrical terms are balanced to give a minimum root-means-square error. And so, an aspherical optical surface represented by different high-order spherical aberrations can be used to increase the depth of field. Therefore, the effective power can be defined only by the defocus term as $$P_{eff} = -\frac{4\sqrt{3} \, a_2^0}{R^2}. \quad \text{(Eq. 20)}$$

where R stands for the instantaneous pupil radius in millimeters when the instantaneous coefficient of defocus term $a_2^0$ is given in micrometers to get the effective power of the diopters. If a wavefront map is defined in radius R with a set of Zernike polynomials, when the pupil constricts, the smaller map is then redefined with a new set of Zernike polynomials, and it will have a set of Zernike coefficients that is different from the original set.

If only the defocus term (n=2, m=0) is considered, Eq. (18) becomes $$b_2^0 = \epsilon^2 \left[ \begin{array}{c} a_2^0 \sum_{i=1}^{N/2-1} a_{2(i+1)}^0 \sqrt{3(3+2i)} \\ \sum_{j=0}^{i} \frac{(-1)^{i+j}(i+j+2)!}{(i-j)!(j+3)!j!} \epsilon^{2j} \end{array} \right] \quad \text{(Eq. 21)}$$

Taking $a_2^0$ as $b_2^0$ and R as $\epsilon R$ in Eq. (20) and using Eq. (21), the effective power becomes $$P_{eff}(\epsilon) = -\frac{4\sqrt{3}}{R^2} \left[ \begin{array}{c} a_2^0 + \sum_{i=1}^{N/2-1} a_{2(i+1)}^0 \sqrt{3(3+2i)} \times \\ \sum_{j=0}^{i} \frac{(-1)^{i+j}(i+j+2)!}{(i-j)!(j+3)!j!} \epsilon^{2j} \end{array} \right]. \quad \text{(Eq. 22)}$$

Sometimes wavefronts of radially symmetric aspheric optical surfaces are not represented by Zernike polynomials but by power series. In this case, the wavefront is written as $$W(Rr) = \sum_{n=0}^{N/2} a_{2n} r^{2n}, \quad \text{(Eq. 23)}$$

where R stands for the pupil radius, r is the radial variable in polar coordinates that defines the unit circle, and N is the maximum radial power. The coefficients $\{a_{2n}\}$ of the power series of Eq. (23) can be converted into Zernike polynomials so that the effective power can be written as $$P_{eff}(\epsilon) = -\frac{12}{R^2} \sum_{n=1}^{N/2} \frac{n \, \epsilon^{2(n-1)}}{(n+1)(n+2)} a_{2n}. \quad \text{(Eq. 24)}$$

The influence of spherical aberration on refraction may not have previously been quantified analytically. Equation (22) indicates that when higher-order spherical aberrations exist, the effective power is no longer determined only by the defocus term. With Eqs. (22) and (24), it is now possible to evaluate the influence of an aspheric shape on refraction.

A more intuitive approach than that described previously was above used to derive a simpler and nonrecursive formula for calculating a new set of Zernike polynomial expansion coefficients for ocular aberrations when the pupil constricts: A relationship has been established between the effective power and the high-order radially symmetric terms that can be useful for determining the influence of high-order spherical aberrations on refraction. Some or all of the approaches described above may be embodied in methods and systems for measuring optical characteristics (often including wavefront data) of eyes and other optical systems, for generating desired refractive changes (including prescriptions), and/or for implementing refractive changes (including laser eye surgery, contact lenses, intraocular lenses, and the like). Such embodiments may optionally include (and/or make use of) some or all of the structures described above regarding, FIGS. 1-3A, optionally per the exemplary embodiments of FIGS. 4 and 5. A wide variety of alternative embodiments may also be implemented, optionally using any of the wide variety of known eye measurement and refraction altering techniques, new eye measurement and refraction altering techniques which are developed, or a combination of both. Exemplary embodiments may, for example, be used for calculation of effective powers of an eye at differing pupil sizes and/or locations, including those induced by differing viewing distances (and/or other viewing conditions). As explained in more detail US Patent Publication No. 20040169820, the full disclosure of which is incorporated herein by reference, such calculations of effective powers may have advantages for treatment of presbyopia.

Derivation of Equation (18)

Begin with the formula for orders n+2. Expand Eq. (17) as $$b_{n+2}^m = \epsilon^{n+2} a_{n+2}^m - \sqrt{(n+5)(n+3)} \, (\epsilon^{n+2} a_{n+4}^m - b_{n+4}^m) + \quad \text{(Eq. A1)}$$
$$\frac{1}{2}(n+4)\sqrt{(n+7)(n+3)} \, (\epsilon^{n+2} a_{n+6}^m - b_{n+6}^m) -$$
$$\frac{1}{6}(n+5) \times (n+4)\sqrt{(n+9)(n+3)} \, (\epsilon^{n+2} a_{n+8}^m - b_{n+8}^m) +$$
$$\ldots + (-1)^{(N-n)/2-1} \frac{\sqrt{(N+1)(n+3)}}{[(N-n)/2-1]!}[(N+n)/2+1] \times [$$
$$(N+n)/2] \ldots (n+5)(n+4)(\epsilon^{n+2} a_N^m - b_N^m),$$

where it is assume that N−n is even. If N−n is odd, Eq. (A1) becomes $$b_{n+2}^m = \epsilon^{n+2} a_{n+2}^m - \sqrt{(n+5)(n+3)} \, (\epsilon^{n+2} a_{n+4}^m - b_{n+4}^m) + \quad \text{(Eq. A2)}$$
$$\frac{1}{2}(n+4) \times \sqrt{(n+7)(n+3)} \, (\epsilon^{n+2} a_{n+6}^m - b_{n+6}^m) -$$
$$\frac{1}{6}(n+5)(n+4) \times \sqrt{(n+9)(n+3)} \, (\epsilon^{n+2} a_{n+8}^m - b_{n+8}^m) +$$
$$\ldots + (-1)^{(N-n-3)/2} \times \frac{\sqrt{N(n+3)}}{[(N-n-3)/2]!}[(N+n+1)/2] \times [$$
$$(N+n-1)/2] \ldots \times (n+5)(n+4)(\epsilon^{n+2} a_{N-1}^m - b_{N-1}^m),$$

it is assumed for the next two formulas that N−n is even. If N−n is odd, an adjustment similar to that in Eq. (A2) can be done. To simplify the process, formulas for N−n being odd will not be given for the next two cases.

Similarly, for order n+4, the expression becomes $$b_{n+4}^m = \epsilon^{n+4} a_{n+4}^m - \sqrt{(n+7)(n+5)} \, (\epsilon^{n+4} a_{n+6}^m - b_{n+6}^m) + \quad \text{(Eq. A3)}$$
$$\frac{1}{2}(n+6) \times \sqrt{(n+9)(n+5)} \, (\epsilon^{n+4} a_{n+8}^m - b_{n+8}^m) -$$
$$\frac{1}{6}(n+7)(n+6) \times \sqrt{(n+11)(n+5)} \, (\epsilon^{n+4} a_{n+10}^m - b_{n+10}^m) +$$
$$\ldots + (-1)^{(N-n)/2-2} \times \frac{\sqrt{(N+1)(n+5)}}{[(N-n)/2-2]!}[(N+n)/2+2][$$
$$(N+n)/2+1] \ldots \times (n+7)(n+6)(\epsilon^{n+4} a_N^m - b_N^m).$$

And for order n+6, the expression is $$b_{n+6}^m = \epsilon^{n+6} a_{n+6}^m - \sqrt{(n+9)(n+7)} \, (\epsilon^{n+6} a_{n+8}^m - b_{n+8}^m) + \quad \text{(Eq. A4)}$$
$$\frac{1}{2}(n+8) \times \sqrt{(n+11)(n+7)} \, (\epsilon^{n+6} a_{n+10}^m - b_{n+10}^m) -$$
$$\frac{1}{6}(n+9)(n+8) \times \sqrt{(n+11)(n+7)} \, (\epsilon^{n+6} a_{n+12}^m - b_{n+12}^m) +$$
$$\ldots + (-1)^{(N-n)/2-3} \times \frac{\sqrt{(N+1)(n+7)}}{[(N-n)/2-3]!}[(N+n)/2+3][$$
$$(N+n)/2+2] \ldots \times (n+9)(n+8)(\epsilon^{n+6} a_N^m - b_N^m).$$

If this process continues, we would finally obtain either Eq. (12) or Eq. (13) depending on whether N−n is even or odd. With the use of Eqs. (A1)-(A4), Eqs. (12) and (13), and combinations of terms for $a_n^m$, $a_{n+2}^m$, $a_{n+4}^m$, ..., Eq. (16) becomes $$b_n^m = \epsilon^n a_n^m - \sqrt{(n+3)(n+1)} \, \epsilon^n \quad \text{(Eq. A5)}$$
$$(1-\epsilon^2)a_{n+2}^m + \frac{1}{2}[(n+2) - 2(n+3)\epsilon^2 + (n+4)\epsilon^4] \times$$
$$\sqrt{(n+5)(n+1)} \, \epsilon^n a_{n+4}^m -$$
$$\frac{1}{6}[(n+2)(n+3) - 3(n+3)(n+4)\epsilon^2 + 3(n+4)(n+5)\epsilon^4$$
$$-(n+5)(n+6)\epsilon^6]\sqrt{(n+7)(n+1)} \, \epsilon^n a_{n+6}^m + \ldots$$

Noticing that the fraction in each summation term of a Zernike coefficient can be expressed as $(-1)^j/j!$, where j is the order of the summation term, and that the number of expansion into $\epsilon$ with each summation is similar to a binomial expansion with an increasing number of multiplication factors relating to n, we can express a final analytical formula as $$b_n^m = \epsilon^n \left[ a_n^m \sum_{i=1}^{(N-n)/2} a_{n+2i}^m \sqrt{(n+2i+1)(n+1)} \times \sum_{j=0}^{i} \frac{(-1)^{i+j}(n+i+j)!}{(n+j+1)!(i-j)!j!} \epsilon^{2j} \right]. \quad \text{(Eq. A6)}$$

Derivation of Equation (19)

The unnormalized Zernike polynomials can be written as $$Z_i(r, \theta) = R_n^{|m|}(r)\theta^m(\theta), \quad \text{(Eq. B1)}$$

where the unnormalized Zernike radial polynomials are defined as $$R_n^{|m|}(r) = \sum_{s=0}^{(n-|m|)/2} \frac{(-1)^s(n-s)!}{s![(n+m)/2-s]![(n-m)/2-s]!} r^{n-2s}. \quad \text{(Eq. B2)}$$

Following a process similar to that described previously, the recursive formula for unnormalized Zernike coefficients can be derived as $$b_n^m = \epsilon^n a_n^m + \sum_{i=1}^{(N-n)/2} \frac{(-1)^i(n+i)!}{n!i!}(\epsilon^n a_{n+2i}^m - b_{n+2i}^m). \quad \text{(Eq. B3)}$$

With the same process as described in Appendix A, a final nonrecursive formula for unnormalized Zernike coefficients can be written as $$b_n^m = \epsilon^n \left[ a_n^m + (n+1) \sum_{i=1}^{(N-n)/2} a_{n+2i}^m \times \sum_{j=0}^{i} \frac{(-1)^{i+j}(n+i+j)!}{(n+j+1)!(i-j)!j!} \epsilon^{2j} \right].$$ (Eq. B4)

Each of the above calculations may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

As noted above, a variety of output data can be generated by the systems and methods of the present invention. Such outputs may be used for a variety of research, comparison, prediction, diagnostic, and verification operations. The outputs may be evaluated directly, or they may be used as input into the system for further analysis. In some embodiments, the outputs will be used to model the effect of an ocular treatment prior to application. In other embodiments, the outputs will be used to evaluate the effect of an ocular treatment after application. The outputs may also be used to design ocular treatments. Relatedly, it is possible to create treatment tables based on outputs of the instant invention.

While exemplary embodiments have described in some detail for clarity of understanding and by way of example, a variety of adaptations, modifications, and changes will be obvious of those of skill in the art. Hence, the scope of the present invention is limited solely by the appended claims.

What is claimed is:

1. A computer program product for calculating a modified normalized Zernike expansion coefficient for an optical system, the computer program product comprising:
   code for accepting an original normalized Zernike expansion coefficient for the optical system, the original normalized Zernike expansion coefficient associated with a first aperture dimension; and
   code for calculating the modified normalized Zernike expansion coefficient for the optical system, the modified normalized Zernike expansion coefficient associated with a second aperture dimension, wherein the modified normalized Zernike expansion coefficient is calculated based on the original normalized Zernike expansion coefficient scaled by a scaling factor, the scaling factor comprising a ratio of the second aperture dimension to the first aperture dimension, the ratio raised to the power of a factor comprising a radial degree of the coefficient; and
   a computer-readable medium for storing the codes.

2. The computer program product of claim 1, wherein the optical system comprises an optical tissue of a patient, and the first aperture dimension comprises a first pupil dimension.

3. The computer program product of claim 2, wherein the first pupil dimension comprises a first pupil radius.

4. The computer program product of claim 1, wherein the optical system comprises an optical tissue of a patient, and the second aperture dimension comprises a second pupil dimension.

5. The computer program product of claim 4, wherein the second pupil dimension comprises a second pupil radius.

6. The computer program product of claim 1, wherein the first aperture dimension is greater than the second aperture dimension.

7. The computer program product of claim 1, wherein the first aperture dimension comprises a first aperture radius.

8. The computer program product of claim 1, wherein the second aperture dimension comprises a second aperture radius.

9. A computer program product for determining an optical surface model for an optical tissue system of an eye, the computer program product comprising:
   code for accepting a first optical data corresponding to the optical tissue system of the eye, the first optical data comprising a first set of normalized Zernike expansion coefficients corresponding to a first aperture dimension;
   code for calculating a second optical data corresponding to the optical tissue of the eye, the second optical data comprising a second set of normalized Zernike expansion coefficients corresponding to a second aperture dimension, wherein the second set of normalized Zernike expansion coefficient is calculated based on the first set of normalized Zernike expansion coefficients scaled by a sealing factor, the scaling factor comprising a ratio of the second aperture dimension to the first aperture dimension, the ratio raised to the power of a factor comprising a radial degree of the coefficient;
   code for determining the optical surface model based on the second optical data; and
   a computer-readable medium for storing the codes.

10. The computer program product of claim 9, wherein first aperture dimension comprises a first pupil dimension.

11. The computer program product of claim 10, wherein the first pupil dimension comprises a first pupil radius.

12. The computer program product of claim 9, wherein second aperture dimension comprises a second pupil dimension.

13. The computer program product of claim 12, wherein the second pupil dimension comprises a second pupil radius.

14. The computer program product of claim 9, wherein the first aperture dimension is greater than the second aperture dimension.

15. A computer program product for calculating effective powers of an optical system, the computer program product comprising:
   code for calculating a first effective power using a first Zernike expansion coefficient for the optical system, the first Zernike expansion coefficient associated with a first aperture dimension; and
   code for calculating a second effective power using a second Zernike expansion coefficient for the optical system, the second Zernike expansion coefficient associated with a second aperture dimension, scaled relative to the first Zernike expansion coefficient using a scaling factor comprising a ratio of the second aperture dimension to the first aperture dimension raised to a power of a factor comprising a radial degree of the coefficient; and a computer-readable medium for storing the codes.

16. The computer program product of claim 15, wherein the first aperture dimension comprises a first aperture radius and the second aperture dimension comprises a second aperture radius.

17. The computer program product of claim 15, wherein the optical system comprises an optical tissue of a patient.

18. The computer program product of claim 17, wherein the first aperture dimension comprises a first pupil dimension and the second aperture dimension comprises a second pupil dimension.

19. The computer program product of claim 18, wherein the first pupil dimension comprises a first pupil radius and the second pupil dimension comprises a second pupil radius.

20. The computer program product of claim 19, wherein the first pupil radius is greater than the second pupil radius.

* * * * *